US008801670B2

(12) United States Patent
Drontle et al.

(10) Patent No.: US 8,801,670 B2
(45) Date of Patent: Aug. 12, 2014

(54) APPARATUS AND METHOD FOR ACCESSING A SINUS CAVITY

(75) Inventors: John R. Drontle, Monticello, MN (US); Anthony J. Hanson, Eden Prairie, MN (US); Peter T. Keith, St. Paul, MN (US)

(73) Assignee: Entellus Medical, Inc., Plymouth, MN (US)

( * ) Notice: Subject to any disclaimer, the term of this patent is extended or adjusted under 35 U.S.C. 154(b) by 851 days.

(21) Appl. No.: 12/038,719

(22) Filed: Feb. 27, 2008

(65) Prior Publication Data

US 2009/0216196 A1 Aug. 27, 2009

(51) Int. Cl.
*A61M 25/06* (2006.01)

(52) U.S. Cl.
USPC ................................... 604/164.01

(58) Field of Classification Search
USPC ............ 606/79–85, 86 R, 191–196; 433/173, 433/76–82
See application file for complete search history.

(56) References Cited

U.S. PATENT DOCUMENTS

| | | | |
|---|---|---|---|
| 2,525,183 A | 10/1950 | Robison | |
| 3,800,788 A | 4/1974 | White | |
| 4,291,690 A * | 9/1981 | Jessen | 128/207.29 |
| 4,737,141 A | 4/1988 | Spits | |
| 5,024,658 A | 6/1991 | Kozlov et al. | |
| 5,261,818 A * | 11/1993 | Shaw | 433/165 |
| 5,632,762 A | 5/1997 | Myler | |
| 5,964,767 A * | 10/1999 | Tapia et al. | 606/323 |
| 6,018,094 A * | 1/2000 | Fox | 606/191 |
| 6,391,017 B2 * | 5/2002 | Bays | 604/506 |
| 6,491,940 B1 | 12/2002 | Levin | |
| 6,679,886 B2 * | 1/2004 | Weikel et al. | 606/79 |
| 6,851,424 B2 | 2/2005 | Scopton | |
| 7,520,876 B2 | 4/2009 | Ressemann et al. | |
| 7,678,099 B2 | 3/2010 | Ressemann et al. | |
| 7,833,204 B2 * | 11/2010 | Picha | 604/288.01 |
| 7,842,062 B2 | 11/2010 | Keith et al. | |
| 7,879,061 B2 | 2/2011 | Keith et al. | |
| 7,918,871 B2 | 4/2011 | Truitt et al. | |

(Continued)

FOREIGN PATENT DOCUMENTS

| | | |
|---|---|---|
| EP | 0129634 A1 | 1/1985 |
| EP | 1598015 A1 | 11/2005 |
| WO | WO 91/17787 A1 | 11/1991 |
| WO | 2005/086945 A2 | 9/2005 |

OTHER PUBLICATIONS

R. Peterson, Sinus Puncture Therapy; Canine Fossa Puncture Method "How I Do It" Head and Neck, The Laryngoscope 91: Dec. 1981 pp. 2126-2128.

(Continued)

*Primary Examiner* — Christopher Beccia
(74) *Attorney, Agent, or Firm* — Vista IP Law Group LLP

(57) ABSTRACT

A system for accessing a sinus cavity of a subject includes an access tool configured to penetrate into the sinus cavity from a location external the subject. The system further includes an access sheath having a distal tubular portion, a lumen extending through the access sheath and the distal tubular portion and dimensioned to receive the access tool, the distal tubular portion comprising one or more cutting surfaces disposed about an external surface thereof. The one or more cutting surfaces may include a plurality of longitudinally oriented grooves for flutes disposed about the periphery of the distal tubular member.

8 Claims, 11 Drawing Sheets

(56) References Cited

U.S. PATENT DOCUMENTS

| | | | |
|---|---|---|---|
| 8,043,253 B2* | 10/2011 | Kraft et al. | 604/35 |
| 8,241,266 B2 | 8/2012 | Keith et al. | |
| 8,251,999 B2* | 8/2012 | Stearns et al. | 606/80 |
| 8,277,478 B2 | 10/2012 | Drontle et al. | |
| 8,282,667 B2 | 10/2012 | Drontle et al. | |
| 8,348,969 B2 | 1/2013 | Keith et al. | |
| 8,585,728 B2 | 11/2013 | Keith et al. | |
| 2002/0138121 A1 | 9/2002 | Fox | |
| 2005/0240147 A1 | 10/2005 | Makower et al. | |
| 2006/0004323 A1 | 1/2006 | Chang et al. | |
| 2006/0084034 A1* | 4/2006 | Hochman | 433/173 |
| 2006/0100687 A1 | 5/2006 | Fahey et al. | |
| 2007/0250105 A1* | 10/2007 | Ressemann et al. | 606/196 |
| 2008/0015472 A1 | 1/2008 | Ressemann et al. | |
| 2008/0015497 A1 | 1/2008 | Keith et al. | |
| 2008/0015544 A1 | 1/2008 | Keith et al. | |
| 2008/0015626 A1 | 1/2008 | Keith et al. | |
| 2008/0033353 A1 | 2/2008 | Truitt et al. | |
| 2008/0172033 A1 | 7/2008 | Keith et al. | |
| 2008/0243123 A1* | 10/2008 | Gordils Wallis et al. | 606/80 |
| 2010/0211007 A1 | 8/2010 | Lesch, Jr. et al. | |
| 2010/0274222 A1 | 10/2010 | Setliff, III et al. | |
| 2011/0071349 A1 | 3/2011 | Drontle et al. | |
| 2011/0224652 A1 | 9/2011 | Drontle et al. | |
| 2012/0010646 A1 | 1/2012 | Keith et al. | |
| 2012/0071727 A1 | 3/2012 | Hanson et al. | |
| 2012/0283625 A1 | 11/2012 | Keith et al. | |
| 2013/0030458 A1 | 1/2013 | Drontle et al. | |
| 2013/0030459 A1 | 1/2013 | Drontle et al. | |
| 2013/0041463 A1 | 2/2013 | Ressemann | |
| 2013/0072958 A1 | 3/2013 | Ressemann et al. | |
| 2013/0123833 A1 | 5/2013 | Lesch et al. | |

OTHER PUBLICATIONS

T.G.A. Ijaduola, Use of a Foley Catheter for Short-Tem Drainage of Frontal Sinus Surgery, Journ. of Laryngology and Otology, Apr. 1989, vol. 103, pp. 375-378.
A. Gatot et al., Early Treatment of Oribital Floor Fractures with Catheter Balloon in Children, Intl. J. of Ped. Otorhinolaryngology, 21 (1991) 97-101.
D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).
J. M. Robison, Pressure Treatment of Maxillary Sinusitis, J.A.M.A., May 31, 1952, pp. 436-440.
J. M. Robison, Pressure Treatment of Purulent Maxillary Sinusitis, Texas State Journal of Medicine, May 1952, pp. 281-288.
Entellus Medical, 510(k) Letter (Amendment 1) and Attachments D & E, dated Mar. 13, 2008.
PCT International Preliminary Report on Patentability (Chapter I of the Patent Cooperation Treaty) for PCT/US2009/032360, Applicant: Entellus Medical, Inc., Form PCT/IB/326 and 373, dated Aug. 31, 2010 (7 pages).
PCT International Search Report for PCT/US2009/032360, Applicant: Entellus Medical, Inc., Form PCT/ISA/210 and 220, dated Mar. 13, 2009(4 pages).
PCT Written Opinion of the International Search Authority for PCT/US2009/032360, Applicant: Entellus Medical, Inc., Form PCT/ISA/237, dated Mar. 13, 2009 (5 pages).
PCT International Search Report for PCT/US2007/088834, Applicant: Entellus Medical, Inc., Forms PCT/ISA/220 and PCT/ISA/210, dated May 20, 2008 (4 pages).
PCT Written Opinion for PCT/US2007/088834, Applicant: Entellus Medical, Inc., Form PCT/ISA/237, dated May 20, 2008 (10 pages).
Petersen, Robert J., Canine Fossa Puncture, The Laryngoscope Office, Oct. 5, 1972, pp. 369-371.
Elidan, J., MD., Irrigation of the Maxillary Sinus by Canine Fossa Puncture Experience with 202 Patients, Ann Otol Rhinol Laryngol, 92:1983, pp. 528-529.
Gottaman et al., Balloon Dilation of Recurrent Ostial Occlusion of the Frontal Sinus, Gottmann et al. Abstract (B-0453) Mar. 2001, 22 pages.
Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.
Yanagisawa, Eiji, et al., Powered Endoscopic Inferior Meatal Antrostomy Under Canine Fossa Telescopic Guidance, ENT-Ear, Nose & Throat Journal, Sep. 2001, pp. 618-620.
Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.
Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.
Entellus Medical, 501(k) Premarket Notification cover letter and Attachment B: Predicate Device Labeling, dated Aug. 15, 2007.
U.S. Appl. No. 11/623,740, filed Jan. 16, 2007, Inventor: Peter Keith, et al.
U.S. Appl. No. 11/696,936, filed Apr. 5, 2007, Inventor: Peter Keith, et al.
Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).
Folweiler, David S., Nasal Specific Technique as Part of a Chiropractic Approach to Chronic Sinusitis and Sinus Headaches, Journal of Manipulative and Physiological Therapeutics, vol. 18, No. 1, (Jan. 1995).
International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2008 (4 pages).
PCT International Search Report for PCT/US2007/66187, Applicant: Entellus Medical, Inc., Forms PCT/ISA/220 and PCT/ISA/210, dated Apr. 17, 2008 (5 pages).
PCT Written Opinion for PCT/US2007/66187, Applicant: Entellus Medical, Inc., Form PCT/ISA/237, dated Apr. 17, 2008 (5 pages).

* cited by examiner

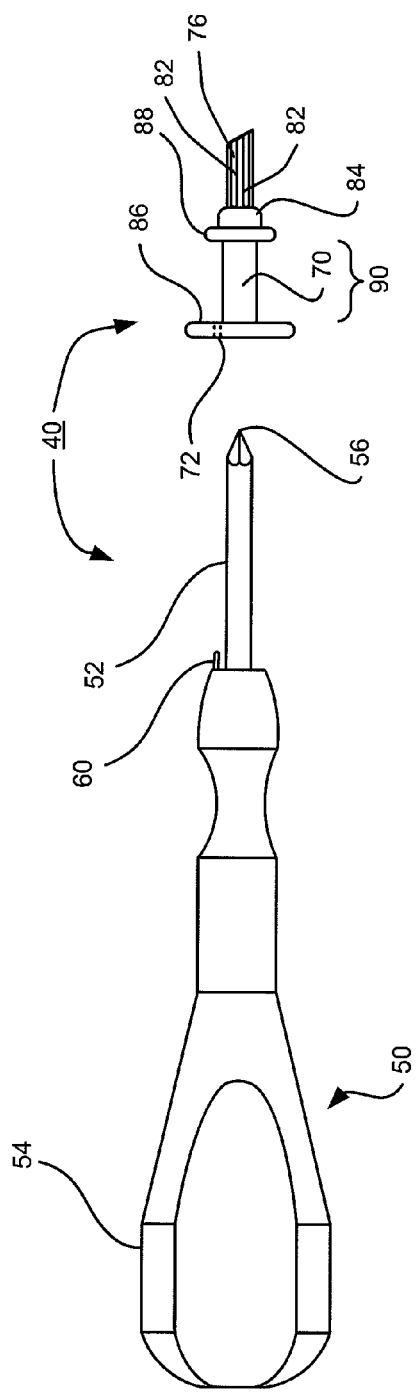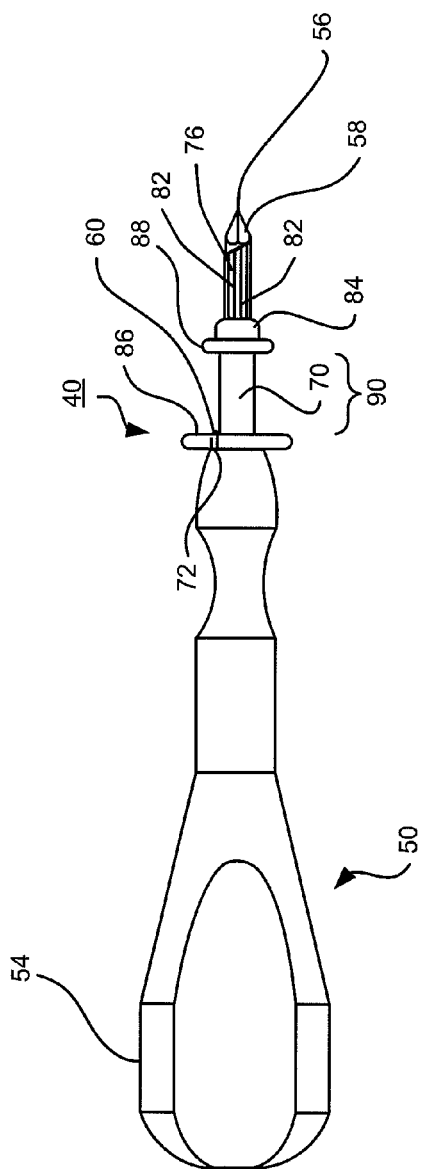
FIG. 3A
FIG. 3B

APPARATUS AND METHOD FOR ACCESSING A SINUS CAVITY

FIELD OF THE INVENTION

The field of the invention generally relates to devices and methods used to gain access to a sinus cavity.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous is interrupted, setting the stage for an infection and/or inflammation of the sinus cavity, i.e., sinusitis. Infection/inflammations of the maxillary and/or ethmoid sinuses make up the vast majority of cases of sinusitis, with far fewer cases involving the sphenoids and frontals. Though many instances of sinusitis may be treatable with antibiotics, but in some cases sinusitis persists for months or more, a condition called chronic sinusitis, and may not respond to medical therapy. Some patients are also prone to multiple episodes of sinusitis in a given period of time, a condition called recurrent sinusitis.

One method of treating sinusitis in a patient includes the process of forming an artificial access passageway into a sinus cavity of the patient in order to access and treat the sinus ostium (outflow tract). For example, an access passageway may be formed in canine fossa region of the patient. One or more working instruments may then be positioned within the access passageway and into the sinus cavity. These instruments may include, for example, an endoscope, cannula, guide wire, balloon dilation catheter, irrigation catheter, aspiration catheter, drug delivery catheter, or the like. U.S. patent application Ser. Nos. 11/379,691 and 11/623,740, which are incorporated by reference as if set forth fully herein, describe various working instruments configured for placement into a sinus cavity via the artificially-formed access passageway.

Generally, once access into the particular sinus cavity (e.g., maxillary sinus) has been gained, and a working device is intended to be placed into the sinus cavity, it is desirable to be able to re-orient the path that such a device takes within the sinus. For example, the access into the sinus may be made by an access tool oriented along a particular angle, but subsequently, a working device may require being oriented along a different path, e.g., a path directed toward the sinus ostium.

There is a clear need for devices and methods that permit external access to a sinus cavity that also enable re-orientation of the access passageway to accommodate the various working instruments that may be employed to treat sinusitis or other condition.

SUMMARY OF THE INVENTION

In a first aspect of the invention, a system for accessing a sinus cavity of a subject includes an access tool configured to penetrate into the sinus cavity from a location external the subject. The system further includes an access sheath having a distal tubular portion, a lumen extending through the distal tubular portion and dimensioned to receive the access tool, the distal tubular portion comprising one or more cutting surfaces disposed about an external surface thereof. The one or more cutting surfaces may include a plurality of longitudinally oriented grooves for flutes disposed about the periphery of the distal tubular member. A proximal hub may be operatively connected to the distal tubular portion, the lumen extending through both the proximal hub and the distal tubular portion.

In a second aspect of the invention, an access sheath for providing access to a sinus cavity includes a proximal hub and a distal tubular portion, a lumen extending through the access sheath from the proximal hub to the distal tubular portion and dimensioned to receive an access tool configured to penetrate into the sinus cavity from an external location, the distal tubular portion comprising one or more cutting surfaces disposed about an external surface thereof. The one or more cutting surfaces may include a plurality of longitudinally oriented grooves for flutes disposed about the periphery of the distal tubular member.

In a third aspect of the invention, a method of accessing a sinus cavity in a subject includes forming an artificial passageway through bone tissue of the subject, placing an access sheath in the artificial passageway in a first orientation, the access sheath having a tubular portion, a lumen extending through the access sheath and the tubular portion, the tubular portion comprising one or more cutting surfaces disposed about an external surface thereof. The access sheath is then re-oriented in a second orientation, wherein the re-orienting comprises rotating the access sheath about a longitudinal axis and panning the access sheath in a direction substantially orthogonal to the longitudinal axis.

Further features and advantages will become apparent upon review of the following drawings and description of the preferred embodiments.

BRIEF DESCRIPTION OF THE DRAWINGS

FIG. 3A illustrates an exemplary system for accessing a sinus cavity of a subject according to one embodiment. The system includes an access tool and an access sheath.

FIG. 3B illustrates the system of FIG. 3A wherein the access tool is positioned within a central lumen of the access sheath.

FIG. 6 further illustrates that the access tool and access sheath may be rotated or advanced in the axial direction as illustrated by the arrows in FIG. 6.

DETAILED DESCRIPTION OF THE ILLUSTRATED EMBODIMENTS

Figure 1:
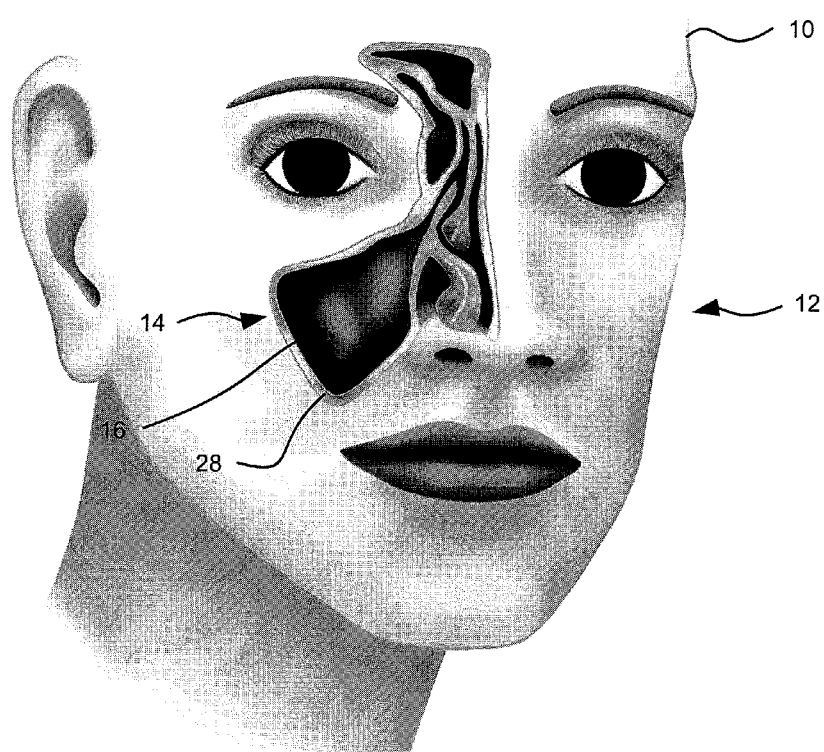
FIG. 1 illustrates a human head showing a partial section view of the subject's nasal and paranasal structures on one side. The maxillary sinus is illustrated.

FIG. 1 illustrates the head 10 of a subject 12 showing a partial section view of the subject's nasal and paranasal structures 14 on one side. The maxillary sinus 16 is the largest sinus cavity in FIG. 1. In one aspect of the invention, the system and method described herein may be used to access the maxillary sinus 16 from a location that is external to the subject 12. For instance, as explained in more detail below, access to the maxillary sinus 16 may be accomplished via an artificial passageway formed in the bone tissue 28 of the subject 12. The bone tissue 28 that is to be traversed may include, for instance, the canine fossa region 26 (not shown in FIG. 1) of the subject 12. While embodiments described herein may describe access to the maxillary sinus 16 it should be understood that the system may also be employed to access or reach other nasal and paranasal structures 14.

Figure 2:
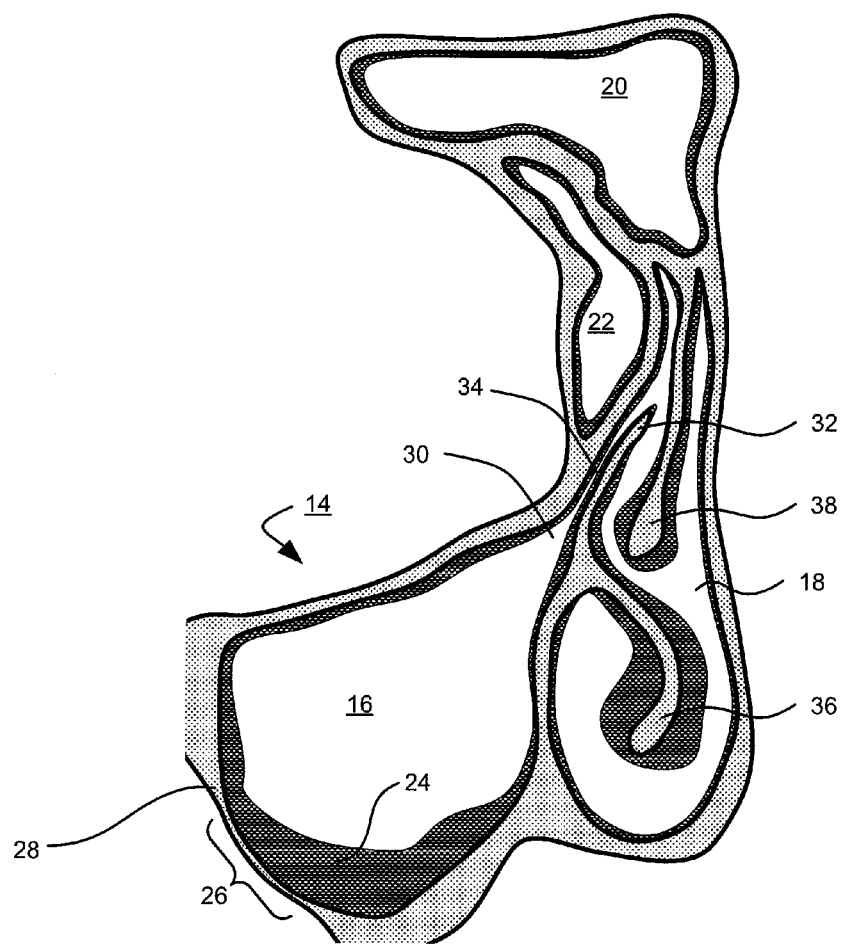
FIG. 2 illustrates a cross-sectional view of the nasal and paranasal structures of a subject, including the nasal cavity, maxillary sinus, frontal sinus, and an ethmoid air cell such as the ethmoid bulla. These anatomical structures are illustrated in a coronal view on the subject's right side. The left side (not shown), has a similar, relatively symmetric structure, but for convenience, only the right side is shown.

FIG. 2 illustrates a cross-sectional view of the nasal and paranasal structures 14 of a subject 12, including the nasal cavity 18, maxillary sinus 16, frontal sinus 20, and an ethmoid air cell 22 such as the ethmoid bulla. These anatomical structures are illustrated in a coronal view on the right side of the subject 12. The left side (not shown), has a similar, relatively symmetric structure, but for convenience, only the left side is shown. As seen in FIG. 2, the maxillary sinus 16 is illustrated with inflamed mucosa 24, which represents a condition known as sinusitis. While treatment of sinusitis is one application of the system and method described herein, the invention is not limited to a particular application or treatment. Rather, the system and method may be employed to access one or more sinus cavities or nasal/paranasal structures 14 whether or not the subject suffers from sinusitis or some other condition.

FIG. 2 further illustrates the canine fossa region 26 of the subject 12. The canine fossa region 26 is a soft tissue/bone structure of the subject 12 generally located near the gum line of the subject 12 near where the canine teeth roots are located. Access via the canine fossa region 26 is advantageous because it provides for direct access to the maxillary sinus 16 via bone tissue 28 that is relatively thin and easy to traverse. FIG. 2 further illustrates the bone 28 tissue of the subject 12 as well as the reduced thickness of bone 28 in the canine fossa region 26. The maxillary sinus 16 drains to the maxillary ostium 30 that, in certain aspects of the invention, may be the desired location for therapeutic treatment using one or more working instruments (not shown in FIG. 2). Additional nasal/paranasal structures 14 illustrated in FIG. 2 include the uncinate process 32, infundibulum 34, inferior turbinate 36, and middle turbinate 38.

FIGS. 3A and 3B illustrate an exemplary system 40 for accessing a sinus cavity of a subject 12 according to one embodiment. The system 40 includes an access tool 50 and an access sheath 70. FIG. 3A illustrates the access tool 50 and the access sheath 70 being separated. FIG. 3B, however, illustrated the access sheath 70 being disposed over a portion of the access tool 50 for form the complete system 40.

The access tool 50, which may also be described as a trocar, includes a shaft portion 52 that is coupled to or otherwise integrated with an optional proximal handle 54. The handle 54 may be configured or dimensioned to aid the user in holding and/or moving the access tool 50 during the accessing method. The handle 54 may be a separate component that is affixed, welded, bonded (e.g., using an adhesive), insert molded, or otherwise secured to a separate shaft 52. Preferably, the shaft 52 further includes surface features such as barbs and longitudinal grooves to further facilitate mechanical engagement between the shaft 52 and the handle 54. Alternatively, the handle 54 and the shaft portion 52 may be constructed as single piece of material stock. The shaft portion 52 may be constructed of a suitable material having a sufficient degree of hardness that enables penetrating movement into the sinus cavity of the patient. For example, the shaft portion 52 may be constructed from a metal such as stainless steel. Of course, it is possible that other "hard" non-metal substances (e.g., polymers, plastics, acrylates, etc.) may be used.

The shaft portion 52 includes a distal tip 56 that includes a cutting tip 58. The cutting tip 58 may include a tri-facet style commonly used in trocars or, alternatively, the cutting tip 58 may include any configuration or design that facilitates cutting through bone 28. The tri-facet cutting tip 58 cuts through bone 28 by means of to-and-fro reciprocating rotation of the shaft 52 (e.g., via handle 54) coupled with a forward-directed force.

In one aspect of the invention, the handle 54 includes a pin 60 that is configured to engage with an aperture 72 in the access sheath 70. As explained in more detail herein, the pin 60 locks the access tool 50 rotationally with respect to the access sheath 70. In this regard, rotation of the access tool 50 will cause a corresponding rotation of the access sheath 70. The aperture 72 and pin 60 may be dimensioned to provide a snug or friction fit such that the access tool 50 and access sheath 70 are held together in the axial direction as well (so that the access tool 50 does not inadvertently de-couple from the access sheath 70).

Figure 4:
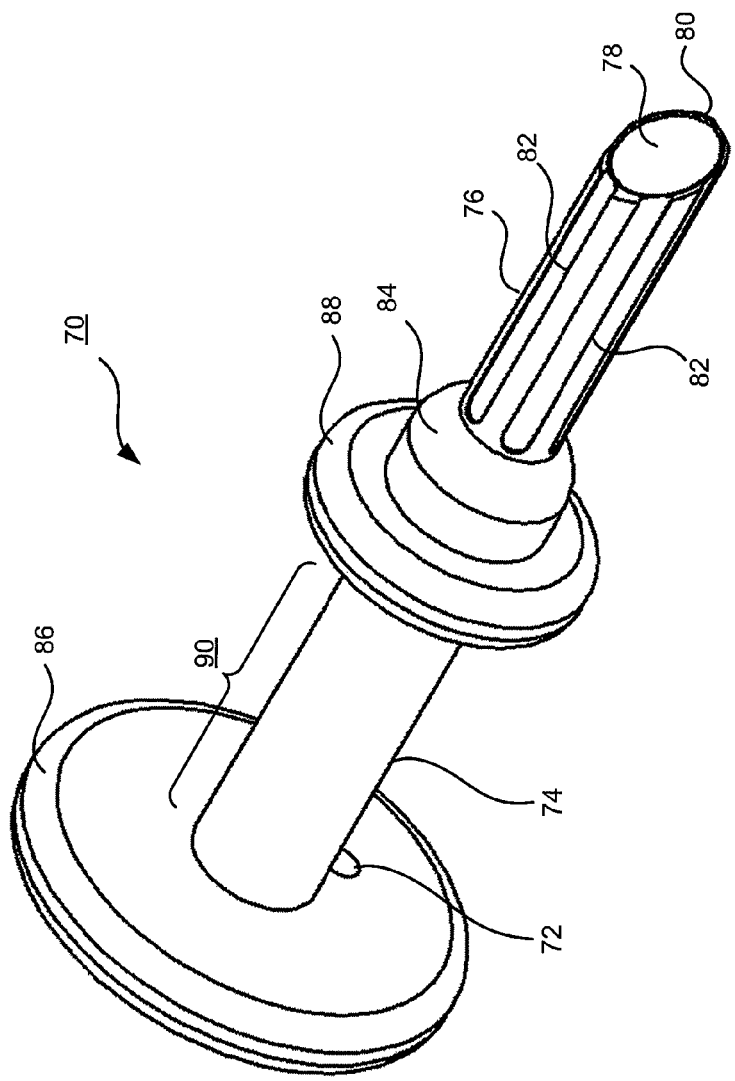
FIG. 4 illustrates a perspective view of the access sheath according to one aspect of the invention.

FIG. 4 is a perspective or isometric view of the access sheath 70. The access sheath 70 includes proximal hub 74 and a distally located tubular member 76. The access sheath 70 includes a lumen 78 that passes from the proximal hub 74 to the distal end of the tubular member 76. The lumen 78 is dimensioned such that the shaft 52 of the access tool 50 may be slid within the lumen 78. The lumen 78 is also dimensioned to permit sliding passage of one or more working instruments (not shown in FIG. 4). In the fully assembled state which is illustrated in FIG. 3B, the distal tip 56 of the shaft portion 52 extends distally from the tubular member 76. In one aspect, the tubular member 76 includes a canted distal tip 80 which aids in the advancement of tubular member 76 through the bone 28 surrounding the sinus cavity. Although not critical, in a preferred embodiment, the inner diameter of the lumen 78 is dimensioned to allow for passage of a "Hopkins Rod" type endoscope, the smallest commonly available size of which is 2.7 mm in diameter. However, smaller and larger lumen diameters are contemplated to fall within the scope of this invention. Both the proximal hub 74 and the distal tubular member 76 may be formed of a single piece of material stock or, alternatively, may be two separate components that are jointed together by any suitable means such as welding, thermal bonding, adhesive bonding, insert molding, mechanical engagement (e.g., screwed into one another) or the like. As best seen in FIGS. 3A, 3B, and 4, the exterior surface of the distal tubular member 76 includes one or more cutting surfaces 82 positioned about the periphery thereof. The cutting surfaces 82 may include a plurality of longitudinally-oriented grooves, flutes, or the like that extend along at least a portion of the length of the distal tubular member 76. The cutting surfaces 82 create longitudinally-oriented cutting surfaces at the outer perimeter of the distal tubular member 76 and permit the user to ream or "side-cut" the artificial passageway 100 to re-orient the system 40 after initial access is made to the sinus cavity. Alternatively, the outer surface of the distal tubular member 76 could include an abrasive (not shown). However, in a preferred embodiment, longitudinally extending grooves 82 are utilized, as they provide "space" for the reamed or side-cut bone material to reside in as the cutting surfaces are utilized.

In one aspect, the cutting surfaces 82 may be milled into the body of the distal tubular member 76. The distal tubular member 76 may be made of a suitably hard material such as metal (e.g., stainless steel), plastic, or the like. The canted tip 80 may include a beveled surface such that the outer surface of the tubular member 76 is beveled towards the inner periphery. Also, the inner surface of the tubular member 76 may be somewhat beveled or "de-burred" so as not to present an inadvertent cutting surface on the inside distal edge of the distal tubular member 76.

Figure 5A:
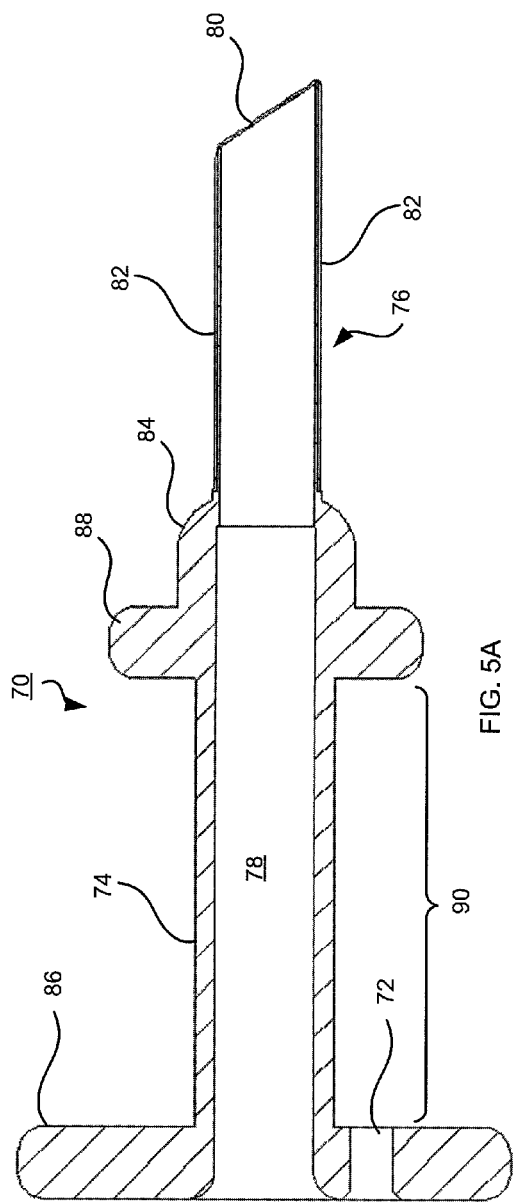
FIG. 5A illustrates a cross-sectional view of the access sheath of FIG. 4 taken along the longitudinal axis of the access sheath.

FIG. 5A illustrates a cross-sectional view of the access sheath 70 of FIG. 4 taken along the longitudinal axis. As seen in FIG. 5A, the proximal hub 74 includes a shoulder portion 84 that increases the outer diameter greater than the shaft portion 52 of the access tool 50. The shoulder portion 84 acts as a stop to prevent additional distal advancement of the access sheath 70. In one aspect of the invention, the proximal hub 74 includes a proximal flange 86 and a distal flange 88 that extend about the periphery of the proximal hub 74. The proximal flange 86 includes the aperture 72 configured to receive the mating pin 60 located on the handle 54 of the access tool 50 (or other pin located on working instrument or the like). A gap 90 is formed between the proximal flange 86 and the distal flange 88 and may be used as a rest that receives the lip of the subject 12 when the system 40 is used to gain access to the maxillary sinus 16 via the canine fossa region 26.

Figure 5B:
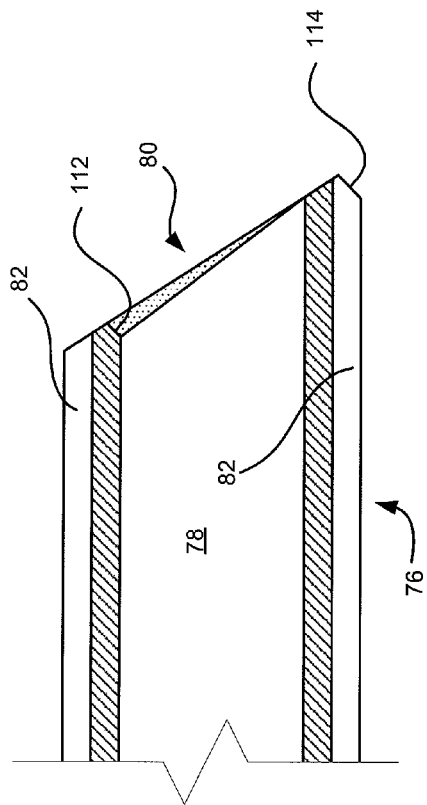
FIG. 5B illustrates a magnified cross-sectional view of the distal end of the access sheath of FIG. 5A.
Figure 6:
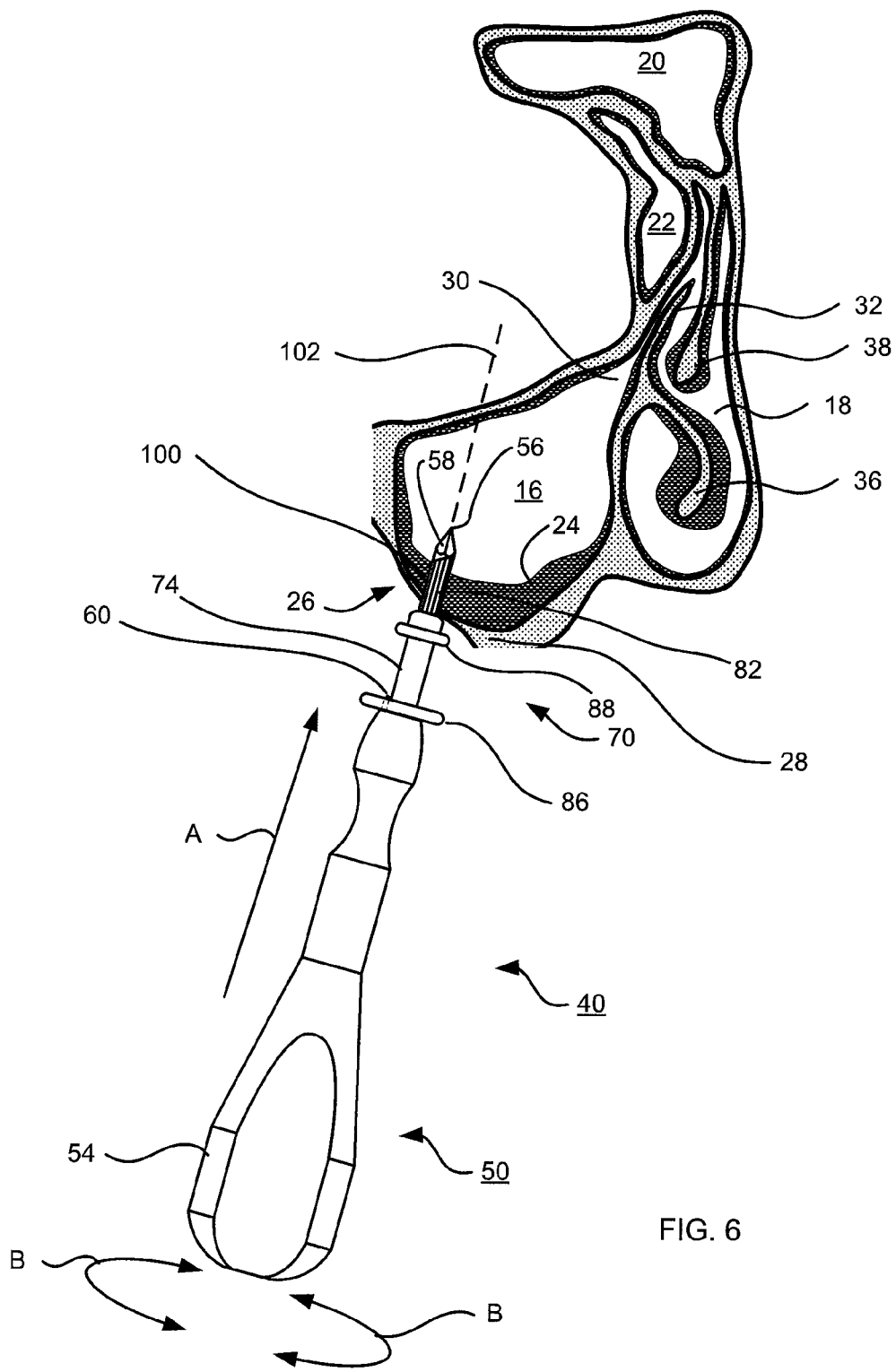
FIG. 6 illustrates a system for accessing a sinus cavity that has been inserted into the canine fossa region of the subject to gain access to the maxillary sinus.

FIG. 5B further illustrates the distal aspect of the access sheath 70 in longitudinal cross-section. The hatched portion represents a thinner or milled portion of the tubular member 76, where as the un-hatched portion represents the full thickness portion of the tubular member 76. Therefore, the outer edge of the full thickness portion becomes a longitudinal cutting edge 82. Inner bevel 112 and outer bevel 114 are more clearly illustrated in FIG. 5B. As can be seen in FIG. 5B, inner bevel 112 gradually "feathers out" and merges with the general angled aspect of the distal tip 80. Outer bevel 114 also gradually merges on the opposite side with the general angled aspect of the distal tip 80. In a preferred embodiment, the outer bevel 114 forms an angle of about 30 degrees with respect to the longitudinal axis of the access sheath 70. FIG. 6 illustrates the system 40 being used to gain access to the maxillary sinus 16 via the canine fossa region 26. Initial access to the maxillary sinus 16 is gained by advancing the access tool 50 and access sheath 70 together distally (in the direction of arrow A) while simultaneously rotating the shaft portion 52 back and forth (in the direction of arrows B). This may be accomplished via the optional handle 54. The distal tip 56 is, in effect, "drilling" through bone 28 to gain access. The mucosa 24 is typically soft, and does not require further drilling to penetrate, but rather will yield upon longitudinal advancement of the access tool 50 and the access sheath 70. In this example, the access tool 50 and access sheath 70 are shown accessing the maxillary sinus 16 through or near the canine fossa region 26. However, it is contemplated that the sinus could be accessed in other areas. Also, other sinuses, e.g. the frontal sinus 20, could be accessed using the system 40 and methods described herein.

In one aspect of the invention, access is obtained into the maxillary sinus 16 while maintaining the access tool 50 and access sheath 70 on a consistent path or angle relative to the subject 12. That is to say, the access tool 50 and access sheath 70 are inserted through the bone 28 in a straight direction along the longitudinal axis 102 of the system 40. The resultant artificial passageway 100 in the bone 28 is therefore shaped in a relatively cylindrical fashion through the wall thickness of the bone 28.

Figure 7:
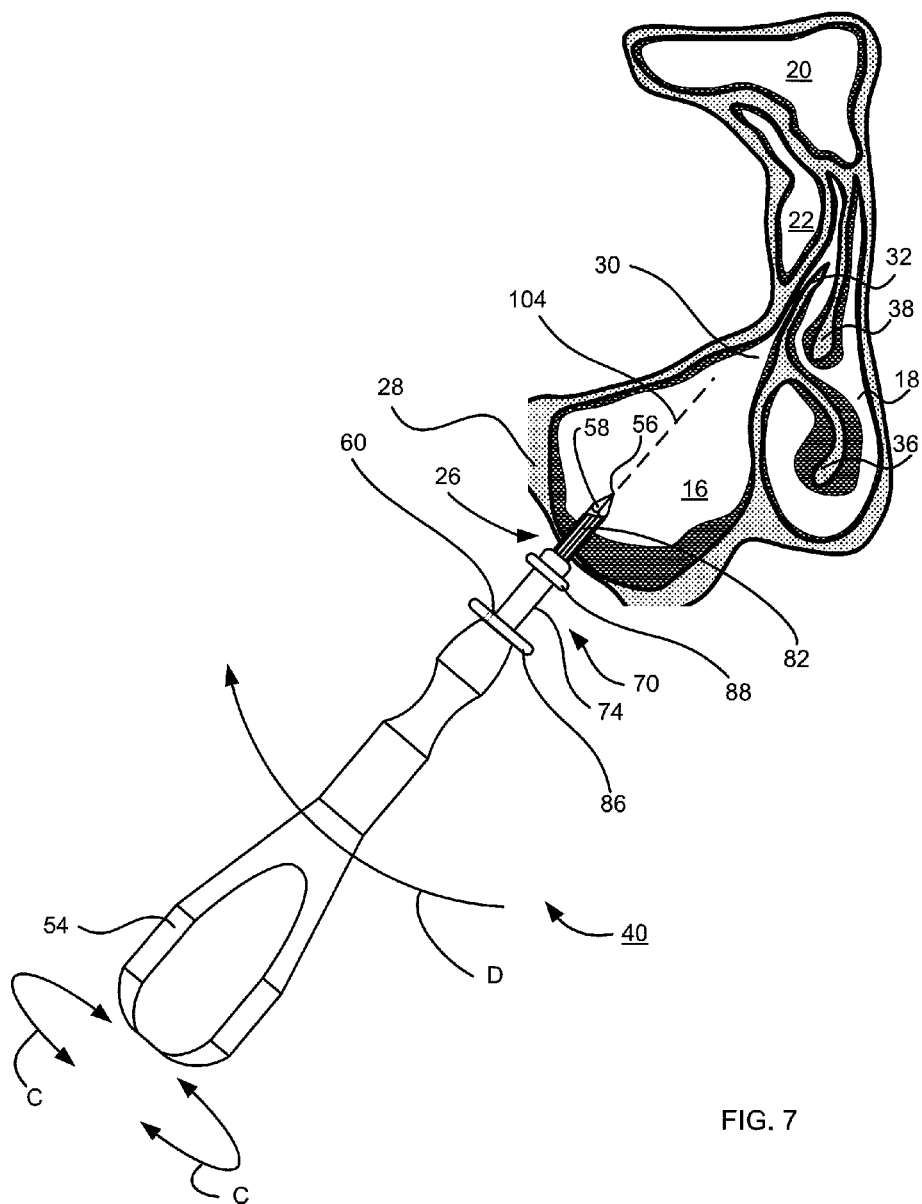
FIG. 7 illustrates the system for accessing a sinus cavity that has been re-oriented to a second orientation through a combination of rotating the access sheath about its longitudinal axis as well as panning motion.

FIG. 6 illustrates the access tool 50 and access sheath 70 being placed into the artificial passageway 100 in a first orientation indicated by dashed line 102. This first orientation of the access tool 50 and access sheath 70 may be used to gain access to the maxillary sinus 16 while avoiding penetrating sensitive tissue or structures with the distal tip 56 of the access tool 50. Next, as seen in FIG. 7, the access sheath 70 may be re-oriented once access has been made. This may be accomplished by rotating the access sheath 70 (in direction of arrow C) while simultaneously panning the access sheath 70 (in direction of arrow D) to change the access sheath 70 into a second orientation indicated by dashed line 104. The panning motion may include moving the access sheath 70 in a direction substantially orthogonal to the longitudinal axis of the access sheath 70. In this second orientation 104, the longitudinal axis 104 of the sheath 70 is tilted toward the maxillary ostium 30 to provide a more "direct shot" toward this area. Of course, the re-oriented angle of the sheath 70 may be directed in other directions other than that illustrated in FIG. 7.

The rotation of the access sheath 70 causes the cutting surface(s) 82 to "ream" or "side-cut" some of the bone 28 defining the original artificial passageway 100. In addition, re-angling or panning the access sheath 70 at the same time the access sheath 70 is rotated causes additional reaming to take place.

Figure 8:
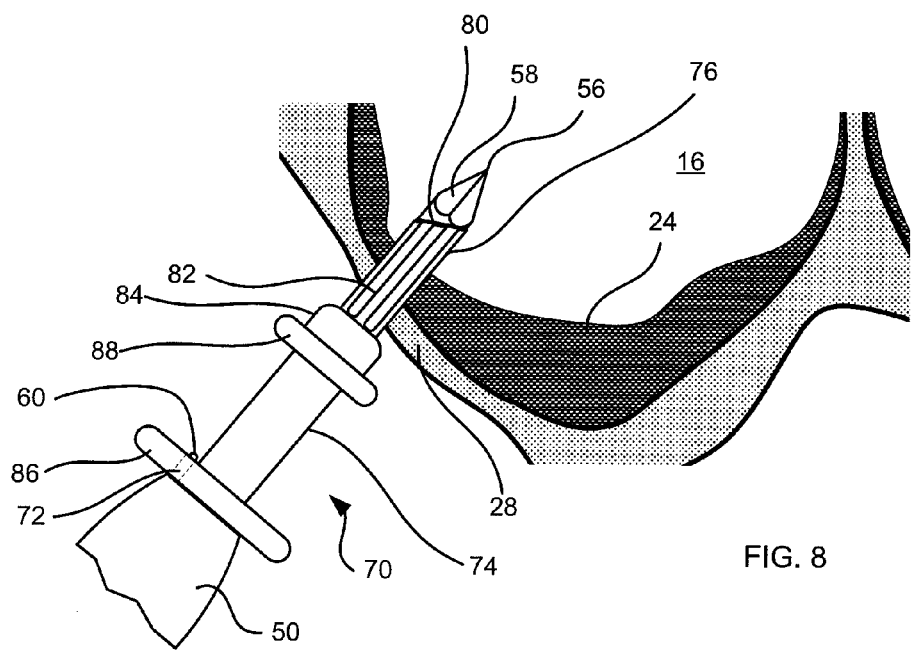
FIG. 8 illustrates the access tool and access sheath traversing bony tissue in the subject to provide access to the maxillary sinus.
Figure 9:
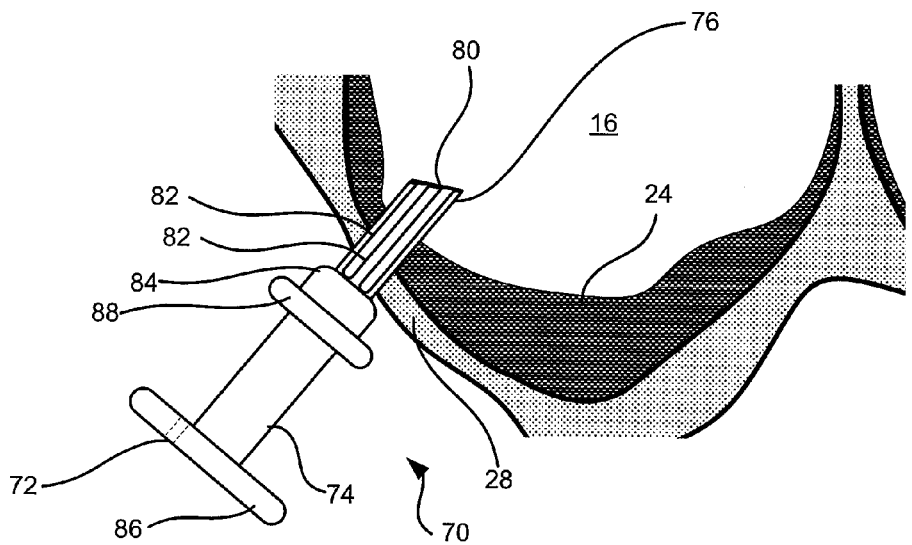
FIG. 9 illustrates the access sheath traversing bony tissue in the subject to provide access to the maxillary sinus. The access tool has been removed.

FIG. 8 is an enlarged view of the access sheath 70 and distal aspects of the access tool 50 after both have entered the maxillary sinus 16. In one aspect of the invention, once the access sheath 70 is at a desired angle (e.g., second orientation 104), the access tool 50 can be removed, leaving the access sheath 70 in the sinus 16, oriented at a desired angle 104, as shown in FIG. 9. For example, it may be desirable to first gain access to the sinus 16 at an initial angle (e.g., orientation 102 in FIG. 6) which avoids the potential for interfering with certain structure(s) associated with the sinus 16, such as the nasal wall or the orbit, or at an angle which is more orthogonal to the surface of the bone 28. Such an orientation may not be the most favorable for subsequent uses of the access sheath 70, however. Since the initial access is essentially "blind", it may be safer to perform this initial access across the bone 28 at a first angle or orientation 102, and then once inside the sinus cavity 16 or at any time thereafter, re-orient the angle of the access sheath 70 to a second desired orientation 104. By way of specific example, the first orientation 102 may be in a generally anterior-posterior direction relative to subject 12. This orientation generally minimizes the chance that the trocar tip 56 will "skate" across the surface of the bone 28 during initial access to the maxillary sinus 16. Thereafter, the second orientation 104 can be made to be more in line with the ostium 30.

While FIG. 7 illustrates the access tool 50 interfacing with the access sheath 70 to adjust the orientation of the access sheath 70, in an alternative configuration, the access sheath 70 may be re-oriented after the access tool 50 has been withdrawn from lumen 78 of the access sheath 70. In this regard, the physician or other skilled artisan may manually manipulate the access sheath 70 via the proximal hub 74 to both rotate the access sheath 70 and provide panning motion to change the angle of rotation of the access sheath 70. In still another aspect of the invention, one or more working instruments 110 may include a pin 60 that interfaces with aperture 72 on the proximal hub 74. Manipulation of the working instrument 110 will result in re-orientation of the sheath 70 as described herein. For example, a guide cannula or the like which may incorporate therein optional imaging functionality may be positioned into the access sheath 70 after placement. Manipulation of the guide cannula may then be used to re-orient the access sheath 70.

Figure 10A:
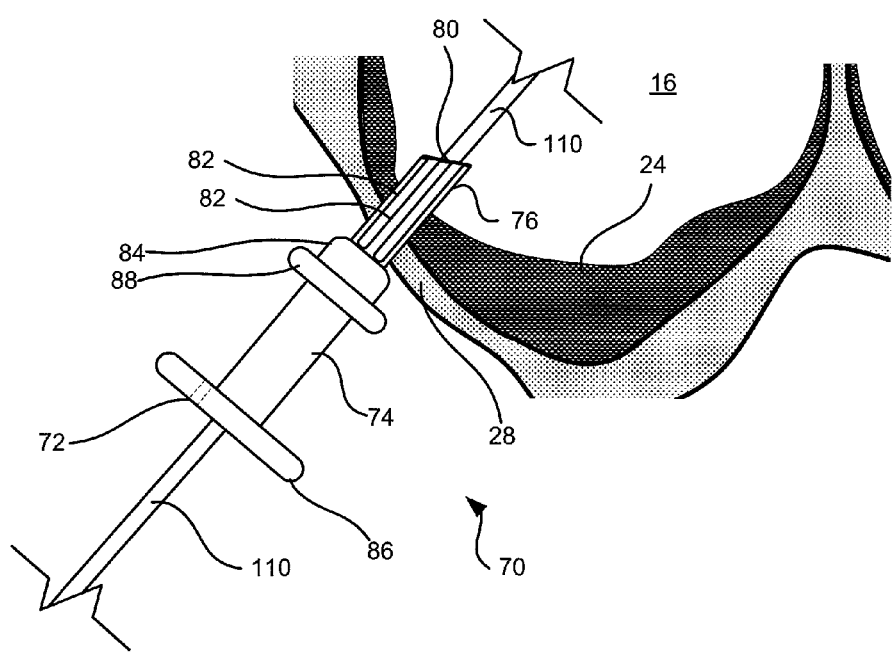
FIG. 10A illustrates a working instrument being positioned within the lumen of the access sheath of FIG. 9.
Figure 10B:
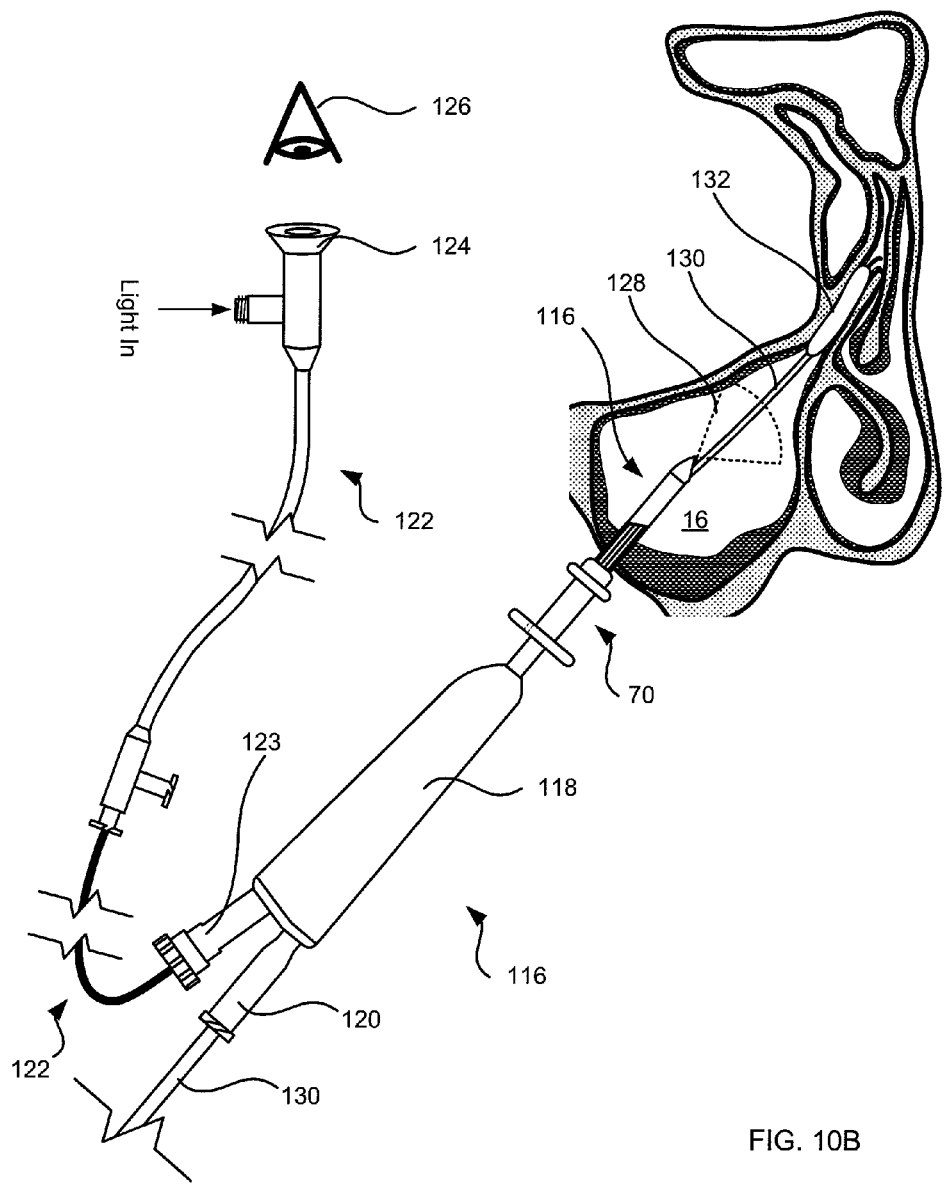
FIG. 10B illustrates a combination of working instruments being positioned within the lumen of an access sheath of FIG. 9. The working instruments may include a cannula, a balloon dilation catheter, and a visualization tool such as an endoscope.

FIGS. 10A and 10B illustrate various working instruments 110 being disposed in the access sheath 70. The working instruments 110 may include any number of therapeutic or diagnostic devices, either individually or in combination. These include, by way of example, an endoscope, a cannula, a guide wire, a balloon dilation catheter, an irrigation catheter, an aspiration catheter, and a drug delivery catheter. In the example where a the working instrument 110 includes a balloon dilation catheter that is intended to be delivered through the access sheath 70, an endoscope can be used to identify the position of the maxillary ostium 30, and then subsequent re-orientation of the access sheath 70 can be performed to align it with the maxillary ostium 30, allowing easier passage and delivery of the balloon catheter. For example, the endoscope 110 may have a pin 60 disposed thereon that interfaces with the aperture 72 on the proximal hub 74. This would permit re-orientation of the access sheath 70 under simultaneous or intermittent visualization.

FIG. 10B illustrates a specific combination of working instruments 110 being utilized in conjunction with the re-orientable access sheath 70. This example is not intended to limit the scope of working instruments 110 that could make use of the invention. These working instruments 110 in this example are similar to those described in connection with prior filed U.S. patent application Ser. No. 11/623,740, and include a cannula 116, a balloon dilation catheter 130, and an endoscope 122. In a preferred embodiment, the cannula 116 includes a handle 118, and two lumens, a first lumen accessible via a balloon catheter port 120, and a second lumen accessible via an endoscope port 123. The endoscope 122 is preferably a flexible small diameter fiberscope, such as a Storz model 11565. The endoscope 122 allows for visualization 128 of the ostium 30 via an eyepiece 124 and/or camera 126 to facilitate guiding a balloon dilation catheter 130 into the ostium 30. Once in position, the dilation balloon 132 is inflated to widen the ostium 30 and adjacent structures as a treatment for sinusitis. In this embodiment, the general orientation 104 (with reference to FIG. 7) of the access sheath 70 is preferably along a line towards the ostium 30, which may be different from a first orientation 102.

Figure 11:
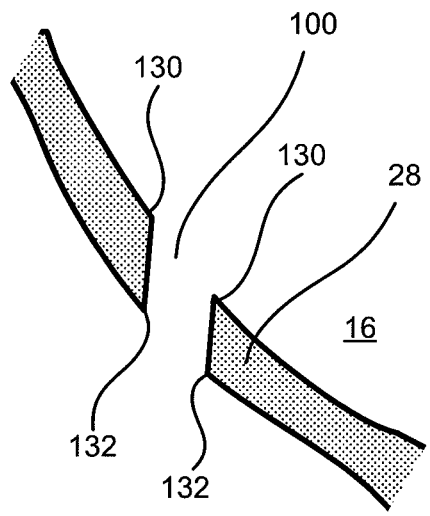
FIG. 11 illustrates a cross-sectional view of a sinus cavity having an access passageway formed therein. The access passageway is shown in the state when the access sheath is in the first or initial orientation.
Figure 12:
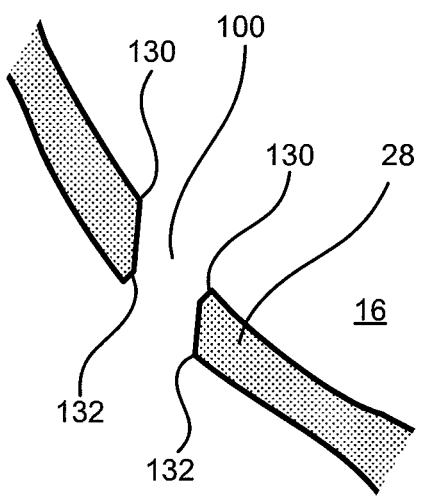
FIG. 12 illustrates a cross-sectional view of a sinus cavity having an access passageway formed therein. The access passageway is shown in the state when the access sheath is in the re-oriented or second orientation.

FIG. 11 illustrates the artificial passageway 100 created in the bone 28 when the initial access is made with the system 40 described herein. This initial access may be made a first orientation 102 as illustrated in FIG. 6. As seen in FIG. 11, the artificial passageway 100 has a generally cylindrical shape with sharp edges 130 formed on diagonally opposite corners 130, 132. In contrast, FIG. 12 illustrates the artificial passageway 100 after the access sheath 70 has been "re-oriented" to a second orientation (e.g., orientation 104 in FIG. 7). The cutting surface(s) 82 on the distal tubular member 76 of the access sheath 70 have served to ream away a portion of the inside and outside surfaces of the bone 28 defining the artificial passageway 100. The resultant artificial passageway 100 is not substantially larger, but does allow for the access sheath 70 and any working instrument 110 to be re-oriented to a more desirable angle into the sinus cavity, e.g. in a line towards the ostium 30. As seen in FIG. 12, one set of diagonally opposite corners 130, 132 no longer has the sharp edges but is rather beveled given the re-orientation of the access sheath 70.

While embodiments of the present invention have been shown and described, various modifications may be made without departing from the scope of the present invention. The invention, therefore, should not be limited, except to the following claims, and their equivalents.

What is claimed is:

1. A method of accessing a sinus cavity in a subject comprising:
    forming an artificial passageway through bone tissue of the subject;
    placing an access sheath in the artificial passageway in a first orientation, the access sheath having a tubular portion, a lumen extending through the access sheath and tubular portion, the tubular portion comprising one or more cutting surfaces disposed about an external surface thereof; and
    re-orienting the access sheath in a second orientation, wherein the re-orienting comprises rotating the access sheath about a longitudinal axis and panning the access sheath in a direction substantially orthogonal to the longitudinal axis.

2. The method of claim 1, wherein the access sheath is re-oriented by placing an access tool in the access sheath and rotating and panning the access tool.

3. The method of claim 1, wherein the access sheath is re-oriented by rotating and panning the access sheath without the presence of an access tool.

4. The method of claim 1, wherein the access sheath is re-oriented by placing a working instrument in the access sheath and rotating and panning the working instrument.

5. The method of claim 4, wherein the working instrument is selected from the group consisting of an endoscope, a cannula, a guide wire, a balloon dilation catheter, an irrigation catheter, an aspiration catheter, and a drug delivery catheter.

6. The method of claim 1, wherein the artificial passageway is formed in the canine fossa region of the subject.

7. The method of claim 1, further comprising stabilizing the access sheath in the second orientation.

8. The method of claim 7, wherein the access sheath comprises a proximal hub operatively coupled to the tubular portion, the proximal hub comprising proximal and distal flanges disposed thereon and wherein the access sheath is stabilized by placing the subject's lips between the proximal and distal flanges.

* * * * *